United States Patent [19]

Schlossman

[11] Patent Number: 4,877,604
[45] Date of Patent: Oct. 31, 1989

[54] METHOD OF INCORPORATING COSMETIC PIGMENTS AND BASES INTO PRODUCTS CONTAINING OIL AND WATER PHASES

[76] Inventor: Mitchell L. Schlossman, 454 Prospect Ave., Unit 164, West Orange, N.J. 07052

[21] Appl. No.: 93,575

[22] Filed: Sep. 4, 1987

[51] Int. Cl.$^4$ .............................................. A61K 7/025
[52] U.S. Cl. ......................................... 424/64; 424/63
[58] Field of Search .................................... 424/63, 64

[56] References Cited

U.S. PATENT DOCUMENTS 4,661,343  4/1987  Zabotto et al. ................... 424/63 X
4,710,373  12/1987  Nakamura et al. ............... 424/63 X
4,724,240  2/1988  Abrutyn ........................... 424/63 X Primary Examiner—Thurman K. Page
Attorney, Agent, or Firm—Handal & Morofsky

[57] ABSTRACT

The present invention relates to improved colorizing cosmetics, titanate based pigments therefor and a method of preparing the same.

2 Claims, No Drawings

METHOD OF INCORPORATING COSMETIC PIGMENTS AND BASES INTO PRODUCTS CONTAINING OIL AND WATER PHASES

BACKGROUND ART

Since at least as early as classical times pigments, oils and moisturizing agents, such as water, have been used in cosmetic preparations to improve the appearance of the skin. Artifacts uncovered by archaeologists include numerous spatulas, spoons, and other applicators for applying pigment to the skin. Indeed, the basic formula for a moisturizing agent was developed by no one less than Galen, the ancient physician himself upon his discovery that water and olive oil could be emulsified to form cold cream which may be used as a moisturizing agent. No doubt he was inspired by the widely followed practice among Romans of bathing in water and then applying olive oil to the skin, without drying, in order to lock in the moisture of the bath water remaining in the skin.

In their essentials, even today, cosmetic preparations remain substantially the same consisting as they do of oils, water and, in the case of colorizing cosmetics, pigment.

In order to better understand the invention, it is useful to consider typical procedures followed in the manufacture of liquid makeup systems. As alluded to above, the basic ingredient in any color makeup system is the pigment which is used to impart the desired color. Typically used pigments include, red, brown, russet, black, and yellow iron oxides and titanium dioxide. Such fillers are mixed with extender, such as talc or kaolin. In addition, other materials such as chalk, fish scale, Fuller's earth and magnesium carbonates may be used to achieve special effects.

In addition to simply increasing the volume of the liquid makeup and maintaining a desired powder concentration, extenders also serve the purpose of forming color dispersions which can be adjusted to compensate for color variations in the raw pigment. The pulverization of pigments with materials having apparently relatively low color strength also has the effect of developing latent color in the pigment. Typically such pulverization is accomplished using a micro-pulverizer.

Once a pigment is micro-pulverized with the extender, the same is typically put into a pigment/extender dispersion. At this point the extender and pigment have been mixed in a manner calculated to achieve maximum development of color strength and to match a color standard. In addition, the micropulverization process has also tended to develop some of the latent color and to some extent to reduce apparent differences in raw pigments. Such micro-pulverization also has the effect of reducing differences which occur during the aqueous stage of processing.

The blender, comprising pigments and extenders in a micro-pulverization mixture, is then dispersed into an aqueous phase using high shear mixing or a colloid mill, to form an emulsion. Such emulsion is formed with a heated aqueous phase in a manner well-known in the prior art and generally involving the charging of a main mixer with a part of the water to be used in the aqueous phase together with a suitable wetting agent. Powders (e.g. pigment and extenders) are added to the main mixer and high shear mixing is performed for 15 to 20 minutes. The remainder of the aqueous phase is then charged into the mixer and high shear mixing is changed to fast mixing. At the same time the aqueous phase begins being heated to 85 degrees centigrade. During the heating and fast mixing phase of the process, the appropriate mixing can be achieved with a simple propeller.

When the mix reaches 85 degrees centigrade, mixing with the propeller is stopped. This allows air to rise in the mix. An anti-foaming agent is added to the mix at this time.

A charge of oils and waxes which has been preheated in a steam pan to 85 degrees centigrade is then added to the aqueous phase. The two solutions are then stirred into each other for approximately 15 minutes. Stirring is done at a relatively high speed but the speed must not be so high as to create a vortex. The mixture is maintained at 85 degrees centigrade during stirring.

After the stirring has been completed, the mixture is allowed to cool. When the temperature reaches approximately 40 degrees centigrade, a preservative may be added. When the mixture reaches 35 degrees centigrade, fragrance can be added to the makeup system. Finally, after cooling is completed, the liquid makeup system can be subjected to the appropriate quality control standards for color, feel, and so forth.

Obviously, the process described above is replete with opportunities for error. All handling of the liquid makeup ingredients carries the possibility of microbiological contamination. The longer a process is, the greater the likelihood that product may be adversely affected through drying out of ingredients, contamination of one color with another, heat effects, and so forth. The ideal objective is a simplification and reduction in the number of the steps and a reduction in the duration of steps. Obviously, the successful pursuit of these objectives will also reduce the cost of product, by reducing the manufacturing cost of total products as well as by reducing the quantity of unusable product.

Nevertheless, in the past, the careful use of the above procedure and the incorporation into the makeup system of numerous agents have been required insofar as the essential ingredients of the cosmetic comprise oil and water which by their very nature, cannot easily mix and which, even after mixing, may not have the right feel. Nevertheless, even with the employment of numerous additional ingredients, liquid makeup systems, for example, tend to settle out and degrade after a period of time. Other makeup systems degrade in other ways. In addition, while the feel of a product is initially commercially acceptable, this "feel" will be lost in time. Moreover, even at its best, feel is not as fine and pleasing as the feel of other non-cosmetic materials such as cornstarch, velvet, satin or fur.

DISCLOSURE OF INVENTION

This invention relates to pigmented cosmetic products in cake, cream, liquid or stick form such as eye shadows, foundations, mascaras and moisturizers.

By improving the dispersions of pigments and other cosmetic materials, such as talc, sericites and mica, and maintaining this dispersion, a more uniform and stable product is formed. The uniformity achieved through improved dispersions avoids the necessity to colloid mill the final emulsion to achieve smoothness and homogeneity in oil in water liquid makeup. The stability characteristics of product avoids settling or segregating out of the composition of pigments or other cosmetic material thus increasing the shelf-life of the product.

Additionally, the use of the improved pigments in liquid pigment/color extenders improves the viscosity range giving more uniform extenders thus keeping the viscosity of the final product uniform.

Improved dispersions, uniformity and stability are achieved by treatment of the pigments and other cosmetic material with a titanate coupling agent that renders them hydrophobic and readily dispersible in oil.

The coating does not affect pigment color and allows incorporation of higher pigment content into an anhydrous cosmetic composition producing a smooth, dry feeling makeup with excellent slip and emollient characteristics.

Other advantages to using the treated or coated materials include increased water resistance due to hydrophobic characteristics, reduced need for powder blends, increased smoothness on application of anhydrous and powder blends, better skin adhesion, better appearance of frosted products, less streaking in pressed and anhydrous makeup products and noticeable smoothness and ease of manufacture of compact cream makeup.

BEST MODE FOR CARRYING OUT INVENTION

Treatment of pigments and other cosmetic raw material with titanate coupling agents may be achieved through either one of two basic methods.

The first method of treatment comprises the addition of 0.01–5.0 weight percent (percent of pigment weight) of the liquid titanate coupling agent into an aqueous uniform dispersion of pigments (or other cosmetic raw material) in a Lightnin' type mixer. This dispersion is typically about 15–20% pigment content. The addition of the titanate coupling agent is done at room temperature accompanied by rapid stirring. Stirring is continued after the dispersement of the titanate coupling agent for 30 to 60 minutes. The pigment dispersion is then separated out of the mixture by filtering through a number 1 (one) paper. The pigments are then washed with water while still in the filter and dried in the filter. The dried pigment is then collected by inverting and tapping the filter causing the treated pigment to fall onto a collection tray. The dried, treated pigment is then ground finely [pulverized] in a micropulverizer twice through a #0020 screen.

A typical example of material proportions used in this method of treatment is:

| Titanate Coupling Agent | |
|---|---|
| Isopropyl triisostearoyl titanate | 3 parts by weight |
| Pigment - Titanium dioxide | 200 parts by weight |
| Water | 1000 parts by weight |

The second method of treatment comprises the spraying of the liquid titanate coupling agent onto a fluidized or agitated filler bed of pigments (or other cosmetic raw material). The amount of the liquid titanate used is 0.01 to 5.0 weight percent of the pigments. The sprayed pigments are then transferred to a blender. High shear mixing as accomplished by a Henschel, P-K twin shell blender with intensifier bar or a Littleford Lodige type requires a mixing time of five minutes or less where a ribbon blender would require up to 40 minutes of mixing for adequate treatment. The treated pigments are emptied from the blender onto a collection tray and then finely ground as in the first method.

The titanate coupling agents used are monalkoxy titanates such as isopropyl triisostearoyl titanate and isopropyl dimethacryl isostearoyl titanate and isopropyl dimethacryl isostearoyl titanate and coordinate titanates such as tetraisopropyl (di(dioctyl) phosphito titanate and tetra (2,2 diallyoxymethyl) butyl, di(ditridecyl) phosphito titanate.

The treatment may be applied to both organic and inorganic pigments, talc, sericites, mica and other materials.

An oil/water liquid makeup is particularly well suited for preparation incorporating the inventive method. Such so-called "O/W" makeup system include cream makeup, cream blusher, water/oil cream makeup, water/oil mascara, liquid eyeliner, cream and liquid eye shadow, liquid rouge oil/water and cream rouge oil/water.

EXAMPLE I

A typical oil/water liquid makeup product was prepared using the weight percent of the various ingredients in the column labeled EXAMPLE although the ranges indicated will produce acceptable product.

O/W LIQUID MAKEUP

|  | RANGE | | PERCENT |
|---|---|---|---|
|  | FROM | TO | EXAMPLE |
| Lanolin Alcohol (and) Mineral Oil | 8.00 | 12.00 | 11.50 |
| Synthetic Spermaceti | 2.00 | 4.00 | 3.20 |
| Stearic Acid XXX | 2.00 | 4.00 | 3.50 |
| Glyceryl Monostearate | 1.00 | 3.00 | 1.80 |
| Talc | 1.00 | 3.00 | 2.00 |
| Titanium dioxide | 2.00 | 6.00 | 4.00 |
| Iron Oxides - Yellow | 0.50 | 2.00 | 1.00 |
| Iron Oxides - Red | 0.20 | 0.60 | 0.40 |
| Iron Oxides - Black | 0.05 | 0.25 | 0.15 |
| Propylene Glycol | 10.00 | 15.00 | 12.00 |
| Triethanolamine | 0.50 | 2.00 | 1.00 |
| PE 20 Sorbitan Monolaurate | 0.40 | 0.80 | 0.65 |
| Magnesium Aluminum Silicate | 0.50 | 2.00 | 1.00 |
| Carboxymethyl Cellulose | 0.20 | 0.50 | 0.30 |
| Deionized Water | 50.00 | 60.00 | 57.20 |
| Preservatives and Fragrance | Q.S. | Q.S. | Q.S. |
|  |  |  | 100.00 |

The titanate treated pigments and talc (a carrier for the pigment) are measured into the oil phase (lanolin alcohol and mineral oil which act as a pigment dispersing agent, emollient and aids product application). When emulsified in the normal manner, well-known in the prior art (the deionized water acting as a main vehicle, the stearic acid reacting and becoming saponified with the triethanolamine opacifying and stabilizing the formula, glyceryl monostearate acting as an auxiliary emulsifier and POE 20 sorbitan monolaurate as a nonionic emulsifier and in stabilizing the system) the final emulsion does not require colloid milling to achieve the desired smoothness and homogeneity. (The additional ingredients include: synthetic spermaceti, which improves gloss and builds viscosity; propylene glycol, which as a humectant prevents drying out after application; magnesium aluminum silicate, which, in addition to acting as a suspending agent for the pigments and an anti-settling agent, functions, as a viscosity builder and improver; sodium carboxymethyl cellulose, which acts synergistically with the magnesium aluminum silicate to suspend, stabilize and add to viscosity; and the preservatives and fragrances.)

Colloid milling or high shear mixing of the aqueous phase was avoided as the pigments were not added into the aqueous phase as is most often done with untreated pigments and talcs. In addition, to improve smoothness and texture qualities the liquid makeup produced an unique emollient slip not present when compared to the same formulation made with uncoated pigments and talc. Powder blends could be eliminated using this procedure, cutting down inventories. Potential microbiological contamination problems are eliminated since certain handling steps are eliminated.

Anhydrous makeup benefits from the hydrophobic quality given to the pigments by the inventive method. These anhydrous makeups include solvent mascara, stick makeup, eye shadow, pencils and crayons, cream rouge and pancake makeup.

EXAMPLE II

A typical anhydrous makeup was prepared using the ingredients shown below in the weight percentages given in the column labeled EXAMPLE although the ranges indicated will produce acceptable product.

COMPACT ANHYDROUS MAKEUP

| | RANGE | | PERCENT |
|---|---|---|---|
| | FROM | TO | EXAMPLE |
| Carnauba Wax | 5.00 | 15.00 | 10.00 |
| Mineral Oil 65/75 Vis. | 27.00 | 35.00 | 33.00 |
| Isopropyl Palmitate | 5.00 | 15.00 | 10.00 |
| Silica | 0.25 | 1.00 | 0.50 |
| Cetyl Acetate and Acetylated Lanolin Alcohol | 3.00 | 7.00 | 5.00 |
| Lanolin Alcohol | 2.00 | 4.00 | 3.00 |
| Isopropyl Lanolate | 2.50 | 7.00 | 5.00 |
| Parabens and fragrance | Q.S. | Q.S. | Q.S. |
| Kaolin | 10.00 | 20.00 | 15.00 |
| Titanium Dioxide | 2.50 | 7.00 | 5.00 |
| Iron Oxides - Yellow | 1.00 | 3.00 | 2.00 |
| Iron Oxides - Black | 0.50 | 2.00 | 1.00 |
| Iron Oxides - Red | 0.25 | 0.75 | 0.50 |
| Iron Oxides - Brown | 5.00 | 15.00 | 10.00 |
| | | | 100.00 |

All liquid components are combined at room temperature in a mixer capable of high shear mixing. The dry ingredients are measured into the liquid and mixed using the high shear equipment. Only the pigments in the dry ingredients have been treated with titanate coupling agent(s) as described above. The mineral oil is again a dispersing agent for the pigments and an emollient and skin lubricant. The isopropyl palmitate adds slip and acts to avoid the greasiness due to the high level of mineral oil. The cetyl acetate, lanolin alcohols and isopropyl lanolate aid in dispersing the pigments and make the final product easier to apply. Kaolin gives covering power to the product and increases oil absorption and grease resistance properties. The silica is pyrogenic silica which acts to absorb oils and get the system giving stability to the product. The silica additionally gives a matte film. The parabens are used as preservatives. When the mixture is homogeneous it is heated using a steam bath to a temperature greater than the highest melting point of the various waxes used. The wax is then added and stirred into the mixture at 85° C. using a Lightnin' type mixer. The wax increases the melting point of the final product giving a firmer product. The mixture is then passed through a Kady mill until uniform (i.e., the desired viscosity range is achieved) and poured hot (60°-95° C.) into its intended package.

Use of the titanate-coated pigment aids dispersion and produces a significantly smoother appearing product. The product also has a lower melting point (48° C. versus 51° C.) than a product made with uncoated pigment. As the pigments were titanate-coated, the product floats on water and disperses easily in mineral oil.

Frosted powder blusher can also take advantage of the inventive method of titanate treatment. Frosted powder blushers here include compact rouge, frosted pressed eye shadow and frosted blusher stick.

EXAMPLE III

The frosted powder blusher prepared using the weight percent proportions shown in the column labeled EXAMPLE is a typical product although the ranges indicated will also produce acceptable products.

FROSTED POWDER BLUSHER

| | RANGE | | PERCENT |
|---|---|---|---|
| | FROM | TO | EXAMPLE |
| GROUP I | | | |
| Talc, 1621, ("WC & D") | 58.00 | 66.00 | 63.89 |
| Bismuth Oxychloride | 10.00 | 20.00 | 15.00 |
| Titanium Dioxide (and) Mica | 5.00 | 15.00 | 10.00 |
| D & C Red 30 Aluminum Lake | 0.30 | 0.80 | 0.70 |
| Carmine | 0.05 | 0.20 | 0.10 |
| Iron Oxides - Yellow | 0.25 | 0.75 | 0.50 |
| Iron Oxides - Black | 0.10 | 0.20 | 0.16 |
| Ultramarine Blue | 0.30 | 0.60 | 0.55 |
| Iron Oxides - Red | 0.20 | 0.60 | 0.40 |
| Methyl Paraben | 0.30 | 0.60 | 0.45 |
| Propyl Paraben | 0.02 | 0.06 | 0.05 |
| Imidazolidinyl Urea | 0.10 | 0.40 | 0.20 |
| GROUP II | | | |
| "Dow" Corning Fluid 360 Silicone | 2.00 | 4.00 | 3.25 |
| Mineral Oil 65/75 Vis. | 3.00 | 7.00 | 4.75 |
| | | | 100.00 |

All Group I ingredients are mixed until uniform in a ribbon blender or a twin shell blender at room temperature. The pigments and talc used have been treated with titanate coupling agent(s) and function in this formula as in EXAMPLE I. The bismuth oxychloride is a pearlescent material adding frost and highlights to the cheek area when the product is used. The titanium dioxide and mica function in the same manner as the bismuth oxychloride except the pearl is flaky and particular. The parabens and urea are preservatives. When these ingredients have been mixed shade adjustments are then made, once again blending until uniform. THe use of titanate treated pigments and talc make pulverization (normally done twice through a #0020 screen at this point) unnecessary before the addition of Group II ingredients. Group II ingredients are added slowly to Group I mixture while mixing. (The silicone and mineral oil function as binders, a pressing aid and give the final product water resistance.) This mixing then continues for another 1014 15 minutes, once again at room temperature, after which the mixture is milled twice through a #0020 screen.

In the prior art this milling would have been done with uncoated pigments and talc along with two previous pulverizations. Aside from omitting pulverizations the use of coated pigments allows for easier color matching, affords a cleaner and frostier appearance to the final product and gives its application a creamier feel.

EXAMPLE IV

Pressed eye shadows benefit from the inventive method much in the same way as do the frosted powder blushers. A typical pressed eye shadow formulation, was prepared using the weight percent shown in the column labeled EXAMPLE for each of the various ingredients although the ranges indicated will produce acceptable products.

PRESSED EYE SHADOW

|  | RANGE FROM | TO | PERCENT EXAMPLE |
|---|---|---|---|
| GROUP I |  |  |  |
| Talc | 70.00 | 80.00 | 76.70 |
| Zinc Stearate | 2.00 | 4.00 | 3.00 |
| Kaolin | 5.00 | 15.00 | 10.00 |
| Titanium Dioxide | 2.00 | 6.00 | 5.00 |
| Methyl Paraben | 0.30 | 0.60 | 0.45 |
| Propyl Paraben | 0.02 | 0.60 | 0.05 |
| Imidazolidinyl Urea | 0.10 | 0.30 | 0.20 |
| Iron Oxides - Black | 0.01 | 0.05 | 0.03 |
| Iron Oxides - Yellow | 0.03 | 0.08 | 0.07 |
| Bismuth Oxychloride | 1.00 | 2.50 | 1.50 |
| GROUP II |  |  |  |
| "Mineral" Oil 65/75 Vis. | 2.00 | 4.00 | 3.00 |
|  |  |  | 100.00 |

When titanate-coated pigments and talc are used, Group I ingredients only require mixing in a ribbon blender or twin shell binder with intensifier bar at room temperature. The double pulverization of Group I mixture through a #0020 screen, necessary without treated pigments and talc, can be omitted. Final pulverization may only be necessary after the mineral oil of Group II, which act as a binder is added. This addition is done slowly while mixing at room temperature followed by 10-15 minutes additional mixing. Once again a smooth application of the product is achieved through the use of the coated pigments. Likewise, color matching before the addition of the mineral oil is easier. The ingredients used function in the same manner as in the other formulations and the zinc stearate acts to improve smoothness in application and adhesion to eyelids, along with the kaolin it aids in compression.

EXAMPLE V

The manufacture of lipstick benefits through omission of milling steps using the inventive method. A typical lipstick was produced with the treated pigments, titanium dioxide and mica and other ingredients as detailed in the following list of ingredients and the weight percent used is shown in the column labeled EXAMPLE, although the ranges indicated will produce acceptable product.

LIPSTICK

|  | RANGE FROM | TO | PERCENT EXAMPLE |
|---|---|---|---|
| Candelilla Wax | 4.00 | 8.00 | 6.00 |
| Carnauba Wax | 2.00 | 4.00 | 3.00 |
| Ozokerite 170-D | 3.00 | 6.00 | 4.00 |
| Paraffin Wax | 1.00 | 3.00 | 2.00 |
| Yellow Beeswax | 4.00 | 8.00 | 6.00 |
| Lanolin Alcohol | 4.00 | 8.00 | 6.00 |
| Oleyl Alcohol, Deod. | 8.00 | 12.00 | 10.00 |
| BHA | 0.10 | 0.30 | 0.20 |
| Castor Oil U.S.P. | 38.00 | 45.00 | 43.25 |
| D & C Red No. 6 Barium Lake | 1.50 | 3.50 | 2.50 |
| D & C Red No. 7 Calcium Lake | 1.50 | 3.50 | 2.50 |
| Iron Oxides | 0.50 | 1.50 | 1.00 |
| FD & C Blue No. 1 | 0.05 | 1.20 | 0.80 |
| Perfume | 0.50 | 1.00 | 0.75 |
| Titanium Dioxide (and) Mica | 10.00 | 14.00 | 12.00 |
|  |  |  | 100.00 |

Castor oil, a good solvent for bromo acid dyes, when present, and giving a soft emollient feel on the lips, is placed in the main mixer. The castor oil should be heated to 80° C. Heating may be accomplished by use of a steam pan. Slowly mix the treated pigments and the dyes into the castor oil using a Lightnin' mixer under high speed or Cowles type dissolver for 30-60 minutes. The candelilla wax, which gives the lipstick hardness, rigidity and high gloss, carnauba wax, used to raise the melting point and impart rigidity, beeswax, which adds tack and improves the molding and binding properties, ozokerite, to raise the melting point and give toughness, paraffin wax, also to raise the melting point, oleyl alcohol good for solvent action on bromo acid dyes when present adds "feel" on lips, and lanolin alcohols, used as a blender or coupling agent aids in achieving product homogeneity are all preheated and melted together at 80°-85° C. by a steam pan or other acceptable means and added to the castor oil, pigment and dye mixture. Mixing is continued through-out the addition of these ingredients. The perfume is added and mixing is continued until mixture is homogeneous. The mixture is strained through a 250 mesh stainless steel screen. The titanium dioxide and mica, pearlescent pigments, (having been previously treated with the titanium coupling agents) are then added and mixing continues until the product is uniform. The lipstick is then cooled and shaped as is customary.

If uncoated pigments are used the color solution in castor oil must be milled before the other ingredients are added. The use of coated titanium dioxide and mica also eliminates the requirement of passing the lipstick solution or mass through a 3-roll mill as is otherwise necessary. The organic pigments ( D & C Red No. 6, D & C No. 7 and F D & C Blue No. 1 in this lipstick example) may be treated with titanate coupling agents, as are the inorganic pigments, or they may be treated with a zirconate coupling agent such as neopentyl (dially) oxyl, tri(dioctyl) phosphito zirconate, to achieve the desired improvement of dispersibility and hydrophobicity.

I claim:

1. A liquid makeup, being smoother and possessing a unique emollient slip when compared to existing liquid make up, the same being comprised of:

|  | RANGE FROM | TO |
|---|---|---|
| lanolin alcohol and/or mineral oil | 8.00 | 12.00 |
| synthetic spermaceti | 2.00 | 4.00 |
| stearic acid (triple pressed) | 2.00 | 4.00 |
| glyceryl monostearate | 1.00 | 3.00 |
| talc treated with titanate coupling agent | 1.00 | 3.00 |
| titanium dioxide | 2.00 | 6.00 |
| iron oxides | 0.75 | 2.85 |
| propylene glycol | 10.00 | 15.00 |

|  | RANGE | |
|---|---|---|
|  | FROM | TO |
| triethanolamine | 0.50 | 2.00 |
| polysorbate 20 | 0.40 | 0.80 |
| magnesium aluminum silicate | 0.50 | 2.00 |
| carboxymethyl cellulose | 0.20 | 0.50 |
| deionized water | 50.00 | 60.00 |
| preservatives and fragrance balance | | |
| | | 100.0 percent by weight, | where the talc and/or titanium dioxide and iron oxides have been treated with a titanate coupling agent.

2. A liquid makeup as in claim 15 wherein said iron oxides are present with the following concentrations expressed in terms of weight percentage said makeup:

|  | RANGE | |
|---|---|---|
|  | FROM | TO |
| iron oxides - yellow, color index #77492 | 0.50 | 2.00 |
| iron oxides - red, color index #77491 | 0.20 | 0.60 |
| iron oxides - black, color index #77499 | 0.05 | 0.25 |

* * * * *